Figure 1:
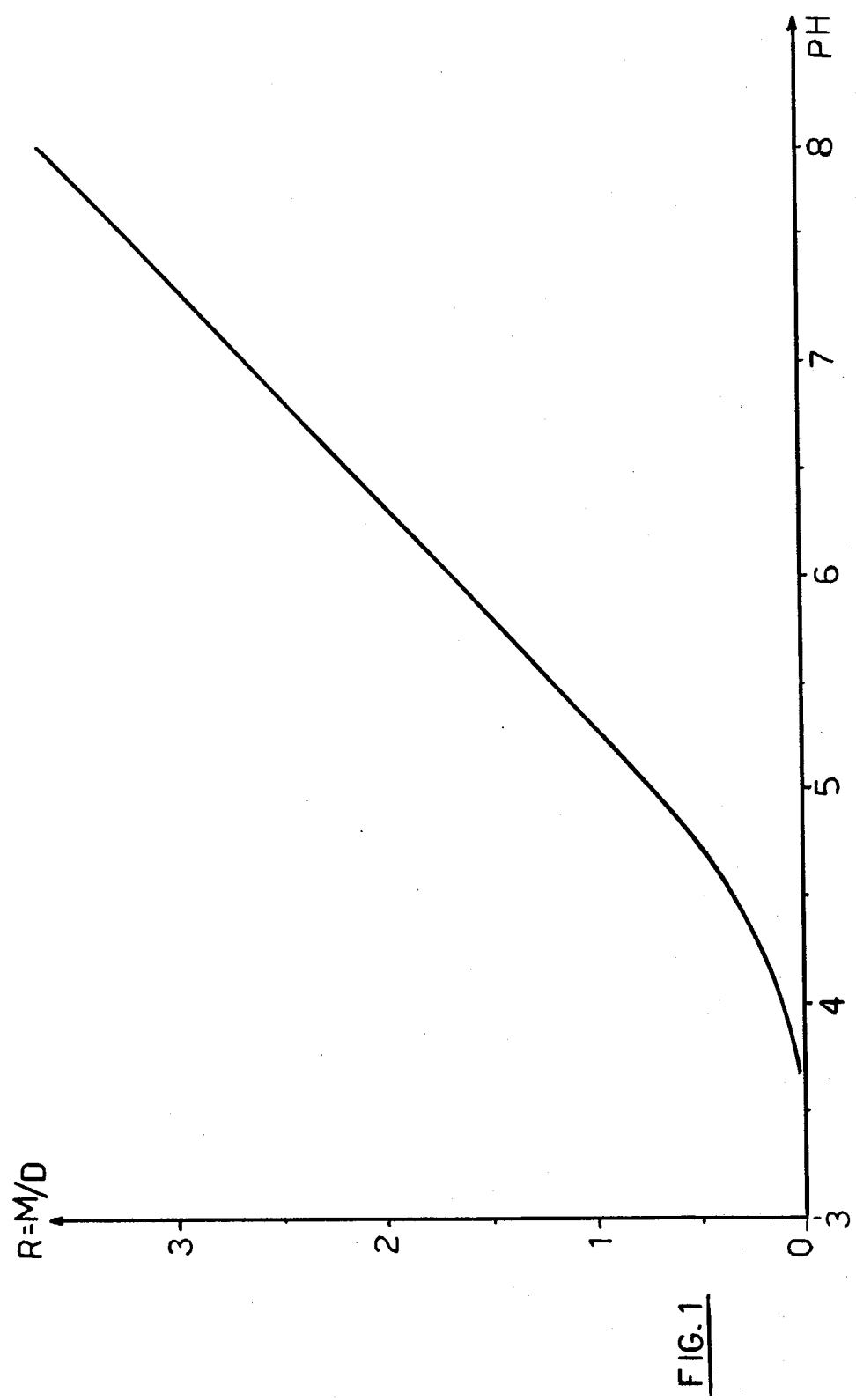

United States Patent [19]
Neri et al.

[11] 3,975,430
[45] Aug. 17, 1976

[54] PROCESS FOR THE PREPARATION OF ALKYLSULPHONATE COMPOUNDS

[75] Inventors: Carlo Neri; Emilio Perrotti, both of San Donato Milanese, Italy

[73] Assignee: Snam Progetti S.p.A., San Donato Milanese, Italy

[22] Filed: Feb. 21, 1975

[21] Appl. No.: 551,609

Related U.S. Application Data

[63] Continuation of Ser. No. 471,707, May 20, 1974, abandoned, which is a continuation of Ser. No. 369,244, June 12, 1973, abandoned.

[30] Foreign Application Priority Data
June 21, 1972 Italy .................................. 25984/72

[52] U.S. Cl. ............................................ 260/513 B
[51] Int. Cl.² ....................................... C07C 143/02
[58] Field of Search ................................ 260/513 B

[56] References Cited
UNITED STATES PATENTS 3,275,681   9/1966    Emerson et al. ................. 260/513 B
3,306,931   2/1967    Adams et al. ................... 260/513 B
3,644,499   2/1972    Murphy et al. .................. 260/513 B
3,706,791   12/1972   Robinette, Jr. ................. 260/513 B
3,729,507   4/1973    Beazley et al. ................. 260/513 B OTHER PUBLICATIONS
Kharasch et al., J. Org. Chem., 3, 175, (1938).
Berry et al., J. Amer. Chem. Soc., 73, 5195, (1951).
Sully, J. Chem. Soc., 1498, (1950).

Primary Examiner—James O. Thomas, Jr.
Assistant Examiner—Nicky Chan
Attorney, Agent, or Firm—Ralph M. Watson

[57] ABSTRACT

Long chain alkyl sulphonates, adapted for use as detergents, are prepared by adding alkali metal bisulphite to a stoichiometric excess of alpha-olefines having from 10 to 20 carbon atoms, in a liquid solvent mixture of alcohol and water having a weight ratio in the range from 1.2 to 2.5, in the presence of oxygen and an oxide or salt of manganese at a temperature not in excess of the boiling point of the solvent mixture, and a pH in the range of 8.5 to 2, wherein the ratio of solvent to olefines is between 6/1 and 2/1.

4 Claims, 1 Drawing Figure

PROCESS FOR THE PREPARATION OF ALKYLSULPHONATE COMPOUNDS

This is a continuation of application Ser. No. 471,707, filed May 20, 1974, now abandoned, which was a continuation of application Ser. No. 369,244, filed June 12, 1973, now abandoned.

The present invention relates to the preparation of alkali metal alkylsulphonates, useful as detergents, by adding alkali metal bisulphites to vinyl double bonds.

More particularly the invention provides an improvement in the process of adding bisulphite to primary olefines by means of a fast reaction system, either batch on continuous, which is started by air and transition metal salts.

Bisulphite addition reactions have been successfully used for producing many alkylsulphonates starting from olefins. Air or other gases containing oxygen, and also peroxide compounds, have been usually employed to start the reaction.

However, it has been found that, when any conventional process started by air is employed for producing an alkylsuphonate from primary olefines, particularly those of higher molecular weight, together with an alkali metal bisulphite, the reaction is very slow and therefore needs very long times for obtaining suitable yields.

For instance the process disclosed in U.S. Pat. No. 2,653,973 requires about from 16 to 40 hours for obtaining reasonable yields of sodium alkylsulphonate. Other known processes started by air need times of a similar order of magnitude.

Some other processes (such as the ones described in German patent 1,098,936, French patent 1,222,105 and U.S. Pat. No. 3,084,186) claim the use of peroxide compounds as promoters: even if remarkable advantages from a kinetic point of view are shown, such processes are not convenient from an economical point of view because of the cost of the promoter. Two recent processes claim the use, as promoters, of nitrates (see for instance "Hydrocarbon Processing" May 1970, page 140) or of peroxides obtainable through a prior oxygenation "in situ" of the olefin itself ("Hydrocarbon Processing" April 1971, page 163).

Both processes have good reaction kinetics, but also have remarkable drawbacks: using nitrates give rise to alkyl-sulphonates containing nitrogen in an amount of about 1 g per alkyl chain: the prior oxygenation of olefins gives rise to recycle products, which are no longer reactive with respect to bisulphite.

Other processes claiming the use of gamma or U.V. radiations do not give good yields and show technological difficulties (French patent 1,453,398 and U.S. Pat. No. 3,450,749).

In any event the secondary reaction of direct oxidation of bisulphite to sodium bisulphate gives rise to a final product very rich in mineral salts, which entails the purification of the final product, besides reagent loss, by means of fractional crystallizations.

We have found that a long chain alkylsulphonate can be produced through a continuous or "batch" system, at practically quantitative yields and average reaction times lower than 1 hour, generally equal to 40 minutes, by adding bisulphite to primary olephines having from 10 to 20 carbon atoms, the addition reaction starting in the presence of salts or oxides of transition metals belonging to the 1st, 7th and 8th groups, such as Fe, Mn, Cu, Co, and the like through a redox system which may be schematized in the following way:

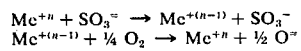

wherein Me is the transition metal;
or

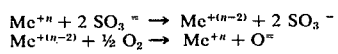

The teachings of the specific scientific papers show these metals strongly catalyze the oxidation of bisulphite to alkaline sulphate and dithionate.

We have surprisingly found that, if the reaction is carried out under suitable reaction conditions, i.e. reagents ratio, solvents type and ratio, temperature and pH, a system is provided which reduces the secondary parasitic reaction of termination to very low levels and, particularly, the formation of inorganic salts.

More particularly, according to the invention, a process is presented for the preparation of alkali metal-sulphonates from $C_{10}$–$C_{20}$ olefines in a solvent constituted by water and alcohol, preferably isopropyl alcohol.

The various components are so proportioned that a suitable excess of olefine (molar ratio $NaHSO_3$/olefines lower than 1 and preferably equal to 0.8 so as to effect the total conversion of the introduced bisulphite), a solvent/olefines ratio by weight ranging between 6/1 and 3/1 and an alcohol/water ratio by weight ranging between 1.2 and 2.5, preferably equal to 1.9, are maintained.

During the reaction the temperature is kept below the boiling temperature of water and, for this purpose, use may be made of an appropriate pressure to keep the system in the liquid phase; when alcohol and water give rise to azeotropic mixtures, it is possible to operate just at the values thereof; when use was made of isopropyl alcohol, we worked at about 80°C which is just the boiling temperature of the water-alcohol mixture.

Therefore use may also be made of temperatures from 20°C to 90°C. The metal promoter is used in amounts of about $10^{-3}$ moles/liter and an air or oxygen flow is contemporaneously sent so that a flow is maintained at to about 0.8 l/h per liter calculated as oxygen. The pH is preferably kept at about 6, but the reaction advantageously proceeds at a pH of from 8.5 to 2.

During the reaction an efficient stirring is maintained in order to allow the emulsifying of the olefine. Bisulphite may be formed in situ from $SO_2$ and alkalies.

The olefine compound employed may belong to any series of alpha-olefines comprised in the $C_{10}$–$C_{20}$ range and may contain also a fraction of internal olefines.

The starting olefine compounds do not need any prior treatment, owing to the fact the same reaction rate is shown by raw olefines, olefines free from peroxides distilled on $FeSO_4$, olefines distilled on bisulphite, olefines recovered from the addition reactions themselves.

Therefore it is clear that the inventive results are not due to starting actions from peroxides present either in the olefines or in the solvent, as the examples will emphasize, wherein we performed the inventive process on olefine fractions and solvents made free from peroxide compounds of any type through boiling and distilling on ferrous sulphate and sodium bisulphite.

The employed promoters are transition metal salts or oxides, preferably iron and manganese oxides ($Fe_2O_3$, $MnO_2$, $Mn_3O_4$); the concentrations range between $10^{-2}$ and $10^{-4}$ M, preferably $10^{-3}$; particularly remarkable advantages are obtained by using $MnO_2$, because it is soluble in bisulphite solutions and can be quantitatively recovered by filtration in the form of $Mn_3O_4$ when, at reaction end, the solution is neutralized under a slight air stream.

The recovered catalyst is still active and therefore can be again utilized. The dry alkylsulphonate contains the catalyst in an amount lower than 5 ppm.

2-propanol (IPA) was the best solvent tested, probably because of the good solvent power with respect to the olefin together with the total miscibility with water.

The $IPA/H_2O$ ratio is very important both as to the reaction kinetics and in order to level at the most the reactivity of the olefines belonging to one fraction.

The best $IPA/H_2O$ ratio is at about 3.5/1.5 by volume and allows a good solubility of the olefines without making the bisulphite insoluble.

The formation of reaction by-products such as $Na_2SO_4$ is very low: the $Na_2SO_4$ content of the dry reaction products is lower than 5% by weight: the preceeding processes never specified the sulphate content, but we experimentally verified that it ranges between 15 and 45% in the claimed processes. The pH control is not unrestrictive provided that it is kept below 8.5; at higher values the reaction stops. The reaction temperature is very important when related to pH; at 80°C the reaction runs out in a favourable way as to kinetics and to selectivity also at pH<8.5 to pH=2; at lower temperatures it is necessary to work in the pH range 5.5 – 8.5; in fact at pH<5.5 at T = 60°C only $Na_2SO_4$ is formed and reaction kinetics are very slow.

The reactions are carried out up to total conversions of bisulphite; the control is performed by means of iodometric titrations during the reaction; pH is continuously controlled by means of a glass electrode coupled with an Ag/AgCl one.

At reaction end the solution is neutralized by NaOH, the catalyst is separated by filtering and the residual olefine is extracted with pentane or steam distilled. The residual hydro-alcoholic solution is evaporated and the solid is dried under vacuum at 100°C. The operation may be carried out in only one stage in spray-dry, sulphonate as a white solid, the solvent and the unreacted olefine recycle being obtained.

The products are in the form of non hygroscopic white powders and do not need a further purification.

The $Na_2SO_4$ content is less than 5% by weight and is the only inorganic impurity present.

The yield on a $C_{15}$ – $C_{18}$ olefine fraction is very high, at average reaction times of about 40 minutes: a value thereof which is not very good but however is easily achievable, is of the order of magnitude of 0.9 mole/h/liter. The inventive process has moreover the following positive aspects:

A. low $Na_2SO_4$ content: using the metal catalysis makes the reaction particularly fast, and therefore decreases the chances for the occurrence of slower reactions, such as the oxidation of bisulphite to sulphate. The sulphate compounds do not exceed 5% by weight:

B. the employment of low air flows, made possible from the fast kinetics, related to a high propagation rate, which decrease the secundary oxidative processes further on account of bisulphite;

C. absolutely unrestrictive pH value, provided that it is lower than 8.5; the reaction may be also carried out at pH lower than 5, without any decrease of kinetics and selectivity, provided that the operations are carried out at 80°C;

D. reactivity of raw, recycled or purified olefines which warrant the catalysis chemistry; im other words it is possible to establish that the reactions is not caused by extraneous substances present in the olefine.

E. catalyst which can be completely recovered and recycled, and also the excess of olefine.

F. chance of obtaining, under appropriate conditions, mixtures of disulphonates and monosulphonates. This is an advantage from three points of view: firstly it allows also the synthesis of the disulphonates besides monosulphonates, secondly the disulphonates are to be preferred because of their solubility with respect to monosuphonates, and then the mixtures of the two compounds may be simply balanced with respect to two components so as to obtain the optimum of properties.

The products obtained by the above described process are white are not hygroscopic and have a very good detergent power and contemporaneously are not toxic and totally biodegradable. Moreover the process, which is the subject of the present invention, makes it possible to obtain products having a solubility higher than the one of the primary linear alkan-sulphonates, because of the presence of more soluble sodium 1,2 alkan-disulphonates, which furthermore significantly act on the critical micelle concentration, as shown by an experimental test of detergency and surface active tension carried out by us. The process makes it possible to balance the monosulphonate-disulphonate ratio through the control of all operating conditions and particularly to pH.

From this point of view a peculiar action is given particularly when the catalysis is performed by means of Fe and Mn as in the hereinafter reported examples.

EXAMPLE 1

Use was made of a glass reactor provided with a stirrer and a Teflon antisloshing baffle, a glass electrode, an air bubbling device, a charging funnel and a reboiling condenser: wherein were dissolved 30 g of $Na_2S_2O_5$ (corresponding to 0.3 mole of $NaHSO_3$) in 250 cc of $H_2O$ and 250 cc of IPA; 100 cc (77 g = 0.3 mole) of a $C_{15}$–$C_{18}$ olefine fraction were added having the following composition by weight of alpha-olefines: $C_{15}$ = 25.04%; $C_{16}$ = 25.04%; $C_{17}$ = 20.67%; $C_{18}$ = 11.68% the difference to 100 consisting of internal olefines.

It was buffered at ph = 6 by 2N NaOH.

The whole was heated under nitrogen to 80°C by means of a heating cover: 50 mg of $MnO_2$ ($0.6\times10^{-3}$ mole) were added and air was begun to flow (1.5 l/h), and the disappearance of bisulphite was monitored iodometrically.

During the reaction pH rose, to 8 – 8.5.

After 1 hour 30 minutes the reaction was over: the solution was hot filtered so as to separate the catalyst and the solution was extracted with four fractions consisting of 80 cc of pentane.

The hydroalcoholic solution was evaporated on a porcelain dish and the solid product was further dried under vacuum at 100°C.

65 g were obtained consisting of a non hygroscopic white powder whose $Na_2SO_4$ content is 5.7% by weight.

From the evaporation of pentane was recovered the olefine excess (35 g) whose composition was $C_{15}$ = 21.78%; $C_{16}$ = 24.56%; $C_{17}$ = 25.54%; $C_{18}$ = 11.88%.

The difference being between the natural weight percentages of the olefines $C_{15}$ and $C_{18}$, expressed as Δ was 11.5%.

EXAMPLE 2

Example 1 was repeated but the solvent consisted of 200 cc of $H_2O$ and 300 cc of IPA.

The reaction time was 1 hour 15 minutes, and the recovered olefine was 31 g having the following composition:

$C_{15}$ = 21.33%; $C_{16}$ = 24.36%; $C_{17}$ = 25.40%; $C_{18}$ = 11.83%. Δ was 10%.

The obtained product contained 5% by weight of $Na_2SO_4$ and was 67 g.

EXAMPLE 3

Example 1 was repeated but the solvent consisted of 150 cc of $H_2O$ and 350 cc of IPA.

The reaction time was 40 minutes and the recovered olefine was 30 g having the following composition:

$C_{15}$ = 23.30%; $C_{16}$ = 24.58%; $C_{17}$ = 24.16%; $C_{18}$ = 11.10%. Δ = 5.5%.

The dry product weighed 70 g and had a $Na_2SO_4$ content equal to 3.8% by weight.

EXAMPLE 4

Example 3 was repeated, but the solution was not buffered at the beginning (pH starting = 4.7).

The reaction time was 40 minutes and pH rose during the reaction to 8.5.

The recovered olefine was 34 g and Δ = 7%.

The product weighed 65 g having a $Na_2SO_4$ content equal to 4.5% by weight.

EXAMPLE 5

Example 1 was repeated but the temperature was kept at 60°C. We did not buffer: starting pH was 4.7, but during the reaction lowered to 1.9 and the reaction rate remarkably decreased; after 3 hours 40 minutes a product was obtained containing 90% by weight of $Na_2SO_4$.

EXAMPLE 6

Example 3 was repeated but use was made of the olefine recovered from foregoing reactions having the composition:

$C_{15}$ = 22.67%; $C_{16}$ = 24.12%; $C_{17}$ = 20.87%; $C_{18}$ = 12.70%.

Also the employed catalyst was recovered from preceding tests. The reaction time was 40 minutes, and 65 g of a product were obtained having a $Na_2SO_4$ content equal to 4.3% by weight.

The recovered olefine was 34 g at a Δ =4%.

EXAMPLE 7

Use was made of a glass reactor provided with a stirrer and a Teflon antisloshing baffle and equipped according to example 1; therein were dissolved 60 g of $Na_2S_2O_5$ (0.6 mole) in 150 cc of $H_2O$ and 350 cc of IPA; 200 cc were added (150 g) of olefine fraction $C_{15} - C_{18}$ and the whole was buffered at a starting pH equal to 5.5.

We heated at 80°C under nitrogen and, when the mixture was at this temperature, air was begun to flow (3 1/h)., The bisulphite disappearance was followed iodometrically: pH was pratically constant and the reaction was over in 2 hours 15 minutes. The separation of the product according to the procedure of example 1 gave rise to 125 g of dry product having a $Na_2SO_4$ content equal to 13.7% by weight.

The recovered olefine was 85 g.

The productivity was 0.24 mole/h/1 calculated on the average molecular weight of the product as monosulphonate.

EXAMPLE 8

Example 7 was repeated but the reaction mixture was added by 100 mg of $MnO_2$ (1.2 · $10^{-3}$ moles).

During the reaction the pH rose to 8.5. The reaction was over in 45 minutes; after having filtered the catalyst, the excess of olefine and the product were separated; 62 g of recovered olefine were obtained, and also 158 g of dry product at a $Na_2SO_4$ content equal to 4.3% by weight. Now the productivity rose to 0.9 mole/h/1, calculated as in example 7. The following examples show the possibility of modifying the monosulphonate/disulphonate ratio through controlling pH at the temperature of 80°C. The graph (FIG. 1) was obtained from a series of experimental tests carried out on $C_{12}$ olefine at different controlled pH; the mono/disulphonate ratio R = M/D was deduced from the C,H,S analyses and compared with the one obtained from titrations of the mixture by means of p-toluidine chlorohydrate.

The two values agreed well with each other.

The following two examples show two bound cases among the performed tests.

EXAMPLE 9

In the same apparatus as the preceding examples were dissolved 30 g of $Na_2S_2O_5$ (0.3 mole) in 150 cc of $H_2O$ and 350 cc of IPA; 100 cc (75 g = 0.45 mole) of $C_{12}$ alpha-olefine and 50 mg (0.6 · $10^{-3}$ mole) of $MnO_2$ were added: the whole was heated under $N_2$ up to 80°C and then air was flowed (flow = 1.5 1/h).

pH was kept at about 4.5 by bubbling $SO_2$ as soon as it was rising.

The reaction was over in 40 minutes. Now pH was brought to 9 by NaOH, the catalyst was filtered and the products were separated.

50 g of olefine and 55 g of dry product containing 5.6% by weight of $Na_2SO_4$ were recovered. From the analysis the product resulted almost entirely consisting of sodium 1,2-dodecandisulphonate.

This product is entirely soluble in water, even if cool.

EXAMPLE 10

The procedure of example 9 was followed but pH was kept at about 6.8 by NaOH.

The reaction was over in 45 minutes and the separation of the products gave 31 g of recovered olefine and 70 g of dry product containing 3.2% by weight of $Na_2SO_4$, having the following approximate compositions: sodium - monalkansulphonate = 210 m.moles, sodium alkandisulphonate-1,2 = 40 m.moles.

Detergency: The inventive products were examined as to detergent property. The detergency measurements were carried out through a method modified with respect to the one described by Harris, Brown "J. Am. Oil Chemists Society" vol. 27 pag. 564–70 (1950).

Use was made of a standard cloth, of the 101 type from Swits EMPA, which was soiled with olive-oil and cinchona-ink.

The washing of the pieces was carried out in a LAUNDER-O-METER (Atlas) apparatus; a glass pot was filled with 210 ml of a solution of the detergent in distilled water, at pH=10, 8 cloth pieces 6 × 4 cm and 10 small stainless steel spheres; the washing was carried out at 50°C for 1 hour while the apparatus was rotating (40 rounds/min).

Every test was doubly realized (2 pots) on 16 pieces as total, and at three different concentrations of active substance (1.2 g/l; 0.69 g/l; 0.3 g/l). After the washing the pieces were rinsed in distilled water, squeezed between two sheets of filter paper, extended on an aluminum sheet and dried at 65°C in an airy oven.

The degree of whiteness was measured from the reflectance by means of an ELREPHO apparatus provided with a "TRISTIMULUS" green filter.

The examinations were performed on both sides of each piece and the detergency was obtained from the reflectance by means of the following expression:

$$D = \frac{R_L - R_{NL}}{R_B - R_{NL}} \cdot 100$$

wherein
$R_L$ = average reflectance of the washed piece;
$R_{NL}$ = average reflectance of the un-washed piece;
$R_B$ = average reflectance of the undirty white piece.

Measurements carried out according to the above method on the sample of example 8 (with catalyst) and on the sample of example 7 (without catalyst) gave the following results

|  | 1.2 g/l | 0.6 g/l | 0.3 g/l |
|---|---|---|---|
| $C_{15}$–$C_{18}$ (with Mn) D% = | 48.2 | 50.8 | 46.3 |
| $C_{15}$–$C_{18}$ (without Mn) D% = | 42.7 | 47.1 | 29.8% |

What we claim is:

1. Process for the production of a long chain alkyl sulphonate, adapted for use as a detergent, by reacting an alkali metal bisulphite with one or more alpha-olefines having from 10 to 20 carbon atoms, wherein the improvement comprises contacting the alkali metal bisulphite with a stoichiometric excess of said alpha-olefine or alpha-olefines in a liquid solvent mixture of isopropyl alcohol and water in the presence of oxygen and a metal promoter selected from the group consisting of $MnO_2$ and $Mn_3O_4$, at a temperature below the boiling point of water, and at a pH from 8.5 to 2, the isopropyl alcohol/water ratio in said solvent mixture being between 1.2 and 2.5 by weight, and the solvent-/olefine ratio being between 6/1 and 3/1 by weight.

2. Process according to claim 1, wherein the alkali metal bisulphite/olefine molar ratio is 0.8.

3. Process according to claim 1, wherein the isopropyl alcohol/water weight ratio in said solvent mixture is 1.9.

4. Process according to claim 1, wherein said bisulphite is prepared in situ by reacting $SO_2$ and alkali.

* * * * *